United States Patent
Chiu et al.

(10) Patent No.: US 10,261,025 B2
(45) Date of Patent: Apr. 16, 2019

(54) WORKPIECE SURFACE DETECTION METHOD AND SYSTEM USING THE SAME

(71) Applicant: INDUSTRIAL TECHNOLOGY RESEARCH INSTITUTE, Hsinchu (TW)

(72) Inventors: Wei-Yao Chiu, Chiayi (TW); Kuo-Feng Hung, Taoyuan (TW); Yu-Ting Lin, Zhudong Township, Hsinchu County (TW); Keng-Hao Chang, Taichung (TW)

(73) Assignee: INDUSTRIAL TECHNOLOGY RESEARCH INSTITUTE, Chutung, Hsinchu (TW)

( * ) Notice: Subject to any disclaimer, the term of this patent is extended or adjusted under 35 U.S.C. 154(b) by 194 days.

(21) Appl. No.: 15/392,325

(22) Filed: Dec. 28, 2016

(65) Prior Publication Data
US 2018/0128750 A1    May 10, 2018

(30) Foreign Application Priority Data
Nov. 4, 2016  (TW) .............................. 105135933 A

(51) Int. Cl.
  *G01N 21/88*  (2006.01)
  *G01N 1/42*  (2006.01)

(52) U.S. Cl.
  CPC ........... *G01N 21/8806* (2013.01); *G01N 1/42* (2013.01)

(58) Field of Classification Search
  CPC ............... G01N 21/88; G01N 21/8803; G01N 21/8806; G01N 2021/8809
  (Continued)

(56) References Cited

U.S. PATENT DOCUMENTS

| 4,314,474 A * | 2/1982 | Dermarderosian .... G01N 21/91 374/4 |
| 6,154,285 A | 11/2000 | Teng et al. |

(Continued)

FOREIGN PATENT DOCUMENTS

| CA | 2587245 C | 12/2013 |
| CN | 101625231 B | 12/2010 |

(Continued)

OTHER PUBLICATIONS

Ulusoy et al., "Robust One-Shot 3D Scanning Using Loopy Belief Propagation," Brown University, Division of Engineering, Providence, RI, 2010 IEEE, pp. 15-22.

(Continued)

*Primary Examiner* — Benjamin R Schmitt
(74) *Attorney, Agent, or Firm* — Muncy, Geissler, Olds & Lowe, P.C.

(57) ABSTRACT

A detecting method for a workpiece surface includes the following steps. Firstly, a workpiece is provided with a first environment, wherein the first environment has a first environmental temperature higher than a first saturation temperature corresponding to an environmental-relative humidity. Then, the workpiece is provided with a second environment, wherein the second environment has a second environmental temperature lower than the first environmental temperature, such that a itself-temperature of the workpiece reduces to a mist temperature, wherein the mist temperature is substantially equal to or higher than the second environmental temperature. Then, the workpiece is provided with a mist environment, wherein the mist environment has a mist-saturation temperature corresponding to a mist-environmental relative humidity is equal to or higher than the mist temperature for misting a surface of the (Continued)

workpiece. Then, the surface of the misted workpiece is detected.

9 Claims, 5 Drawing Sheets

(58) Field of Classification Search
USPC .................. 73/73, 104, 865.6, 865.9, 866
See application file for complete search history.

(56) References Cited

U.S. PATENT DOCUMENTS

| | | | |
|---|---|---|---|
| 6,392,754 | B1 | 5/2002 | Pingel et al. |
| 6,549,288 | B1 | 4/2003 | Migdal et al. |
| 6,856,407 | B2 | 2/2005 | Knighton et al. |
| 7,315,383 | B1 | 1/2008 | Abdollahi |
| 7,507,437 | B2 | 3/2009 | Huang et al. |
| 7,571,061 | B2 | 8/2009 | Cai |
| 8,064,069 | B2 | 11/2011 | Wienand et al. |
| 8,427,656 | B2 | 4/2013 | Hullin et al. |
| 2011/0262877 | A1* | 10/2011 | Katsumata ............... F27B 9/02 432/77 |
| 2017/0052023 | A1* | 2/2017 | Hung ................... G01B 11/24 |

FOREIGN PATENT DOCUMENTS

| | | |
|---|---|---|
| CN | 102607466 A | 7/2012 |
| CN | 102538704 B | 12/2013 |
| CN | 103644860 A | 3/2014 |
| CN | 103743758 A | 4/2014 |
| CN | 203688485 U | 7/2014 |
| CN | 104729428 A | 6/2015 |
| EP | 0065051 A2 | 11/1982 |
| EP | 0290228 B1 | 12/1992 |
| EP | 2526375 A1 | 11/2012 |
| TW | I281024 B | 5/2007 |
| TW | M364878 U | 9/2009 |
| TW | 201003562 A | 1/2010 |
| TW | I324254 B | 5/2010 |
| TW | I502280 B | 10/2015 |
| WO | WO8905707 A1 | 6/1989 |
| WO | WO2011/091264 A1 | 7/2011 |

OTHER PUBLICATIONS

Lange, Robert, "3D Time-of-flight distance measurement with custom solid-state image sensors in CMOS/CCD-technology," Department of Electrical Engineering and Computer Science at University of Siegen, Jun. 28, 2000, 222 pages.

Zeiss Micura, "Maximum Precision for Small Parts," Jul. 1, 2004, www.zeiss.com/metrology/products/systems/bridge-type-cmms/micura.html, 3 pages.

Pankaj et al., "3-D Imaging Techniques and Review of Products," ResearchGate, Conference Paper, Sep. 2013, 6 pages.

KLA Tencor, MicroXAM—100 3D Surface Profilometer, www.kla-tencor.com/Surface-Profiling/microxam-100.html, 2016, 2 pages.

Nikon, "LC15Dx Laser Scanner," www.nikonmetrology.com/en_EU/Products/Laser-Scanning/CMM-scanning/LC15Dx-laser-scanner/ (Key_features); 8 pages.

Geng, Jason, "Structured-light 3D surface imaging: a tutorial," IEEE Intellegent Transportation System Society, published Mar. 31, 2011, pp. 128-160.

Heizmann, Michael, "Brilliant Insights—Deflectometry for the inspection of specular surface," Fraunhofer Institute of Optronics, System Technologies and Image Exploitation IOSB, www.IOSB.fraunhofer.de, 2 pages.

Zhang et al., "Rapid Shape Acquisition Using Color Structured Light and Multi-pass Dynamic Programming," Department of Computer Science and Engineering, University of Washington, pp. 1-13.

* cited by examiner

WORKPIECE SURFACE DETECTION METHOD AND SYSTEM USING THE SAME

CROSS-REFERENCE TO RELATED APPLICATION

This application claims the priority benefit of Taiwan application serial no. 105135933, filed on Nov. 4, 2016. The entirety of the above-mentioned patent application is hereby incorporated by reference herein.

TECHNICAL FIELD

The technical field relates to a detecting method for a workpiece surface and a system using the same, and more particularly to a detecting method for the misted surface of a workpiece and a system using the same thereof.

BACKGROUND

In order to detect defects in a surface of a workpiece with high-reflectivity or to measure a size of the workpiece, a common method is to spray the surface of the workpiece with extinction powders for reducing the reflectivity. After the surface defects and the size are shown, the surface of the workpiece is inspected or measured by way of non-contact imaging technique. However, in such method, the extinction powders must be completely removed after inspecting and measuring, and thus it is very time-consuming and difficult, and easily leads to pollution of the production line. Accordingly, it is difficult to be widely used.

SUMMARY OF THE DISCLOSURE

According to an embodiment of the disclosure, a detecting method for a workpiece surface is provided. The detecting method includes the following steps. A workpiece is provided with a first environment, wherein the first environment has a first environmental temperature higher than a first saturation temperature corresponding to a first environmental relative humidity of the first environment; the workpiece is provided with a second environment, wherein the second environment has a second environmental temperature lower than the first environmental temperature, such that a itself-temperature of the workpiece reduces to a mist temperature, wherein the mist temperature is substantially equal to or higher than the second environmental temperature; the workpiece is provided with a mist environment, wherein the mist environment has a mist-saturation temperature corresponding to a mist-environmental relative humidity is equal to or higher than the mist temperature for misting a surface of the workpiece; and the surface of the misted workpiece is detected.

According to another embodiment of the disclosure, a detecting system for a workpiece surface is provided. The detecting system includes a first air-conditioning module, a second air-conditioning module, a mist air-conditioning module and a detecting module. The first air-conditioning module is configured to provide a workpiece with a first environment, wherein the first environment has a first environmental temperature higher than a first saturation temperature corresponding to a first environmental relative humidity of the first environment. The second air-conditioning module is configured to provide the workpiece with a second environment, wherein the second environment has a second environmental temperature lower than the first environmental temperature, such that a itself-temperature of the workpiece reduces to a mist temperature, wherein the mist temperature is substantially equal to or higher than the second environmental temperature. The mist air-conditioning module is configured to provide the workpiece with a mist environment, wherein the mist environment has a mist-saturation temperature corresponding to a mist-environmental relative humidity is equal to or higher than the mist-temperature for misting a surface of the workpiece. The detecting module is configured to detect the surface of the misted workpiece.

According to another embodiment of the disclosure, a detecting method for a workpiece surface is provided. The detecting method includes the following steps. A workpiece is provided with a first environment, wherein the first environment has a first environmental temperature higher than a first saturation temperature corresponding to a first environmental relative humidity of the first environment; the workpiece is provided with a gas, wherein the gas has a gas-saturation temperature higher than a itself-temperature of the workpiece for misting a surface of the workpiece; and the surface of the misted workpiece is detected.

According to another embodiment of the disclosure, a detecting system for a workpiece surface is provided. The detecting system includes a first air-conditioning module, a gas provider and a detecting module. The first air-conditioning module is configured to provide a workpiece with a first environment, wherein the first environment has a first environmental temperature higher than a first saturation temperature corresponding to a first environmental relative humidity of the first environment. The gas provider is configured to provide the workpiece with a gas, wherein the gas has a gas-saturation temperature higher than an itself-temperature of the workpiece for misting a surface of the workpiece. The detecting module is configured to detect the surface of the misted workpiece.

The above and other aspects of the present disclosure will become better understood with regard to the following detailed description of the preferred but non-limiting embodiment (s). The following description is made with reference to the accompanying drawings.

Figure 1:
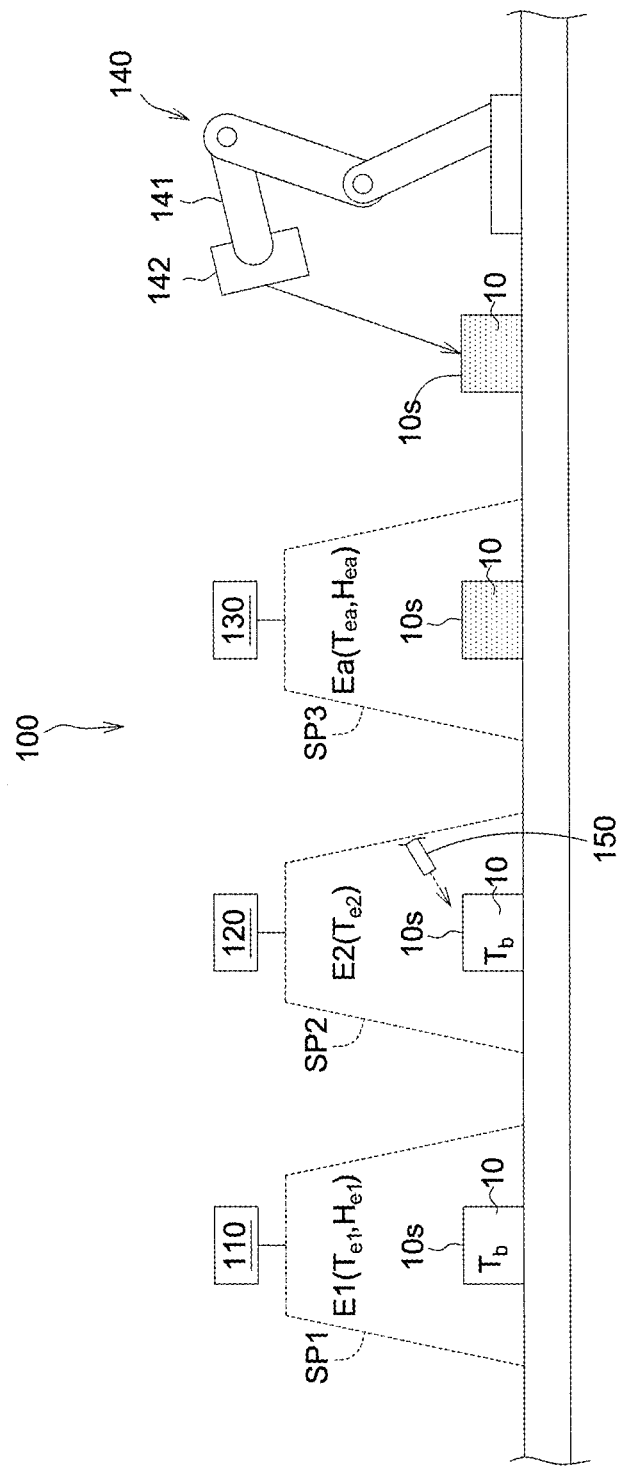
FIG. 1 is schematic diagram showing a detecting system for a workpiece surface according to an embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION OF DISCLOSED EMBODIMENTS

FIG. 1 is schematic diagram showing a diagram of a detecting system 100 for a workpiece surface according to an embodiment of the present disclosure. The detecting system 100 includes a first air-conditioning module 110, a second air-conditioning module 120, a mist air-conditioning module 130, a detecting module 140 and a temperature sensor 150.

In the present embodiment, the first air-conditioning module 110, the second air-conditioning module 120 and the mist air-conditioning module 130 may separately provide the workpiece 10 with a first environment E1, a second environment E2 and a mist environment Ea for changing a temperature and a humidity of the workpiece 10, and misting a surface 10s of the workpiece 10 by the mist environment Ea.

In the present embodiment, the first air-conditioning module 110, the second air-conditioning module 120 and the mist air-conditioning module 130 are disposed within or interconnect with a first space SP1, a second space SP2 and a mist space SP3 respectively for controlling the temperature and the humidity of these spaces. In another embodiment, the first air-conditioning module 110, the second air-conditioning module 120 and the mist air-conditioning module 130 may be disposed within the first space SP1, the second space SP2 and the mist space SP3 respectively. For example, the first space SP1, the second space SP2 and the mist space SP3 are three workstations in a production line or three different spaces in a laboratory.

In another embodiment, the first air-conditioning module 110, the second air-conditioning module 120 and the mist air-conditioning module 130 may be integrated into single air-conditioning module. In this embodiment, the first space SP1, the second space SP2 and the mist space SP3 may be the same space, wherein the single air-conditioning module may provide the same space with different temperature and the humidity at different timing. In addition, the first space SP1, the second space SP2 and/or the mist space SP3 may be a close space or an open space.

Figure 2:
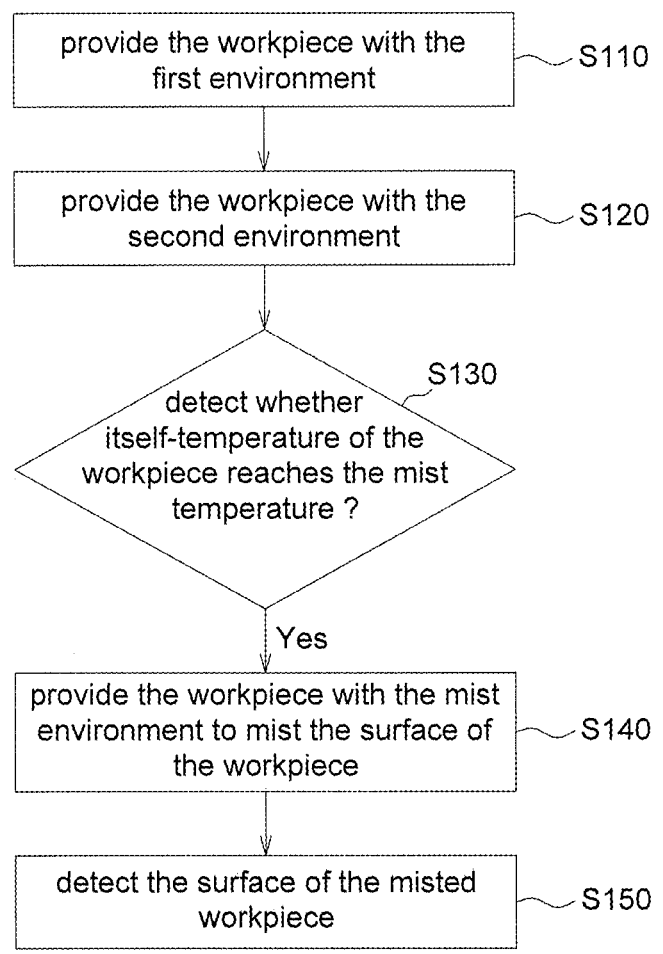
FIG. 2 is schematic diagram showing a flowchart of a detecting method for a workpiece surface according to an embodiment of the present disclosure.

FIG. 2 is schematic diagram showing a flowchart of a detecting method for a workpiece surface according to an embodiment of the present disclosure.

Figure 3:
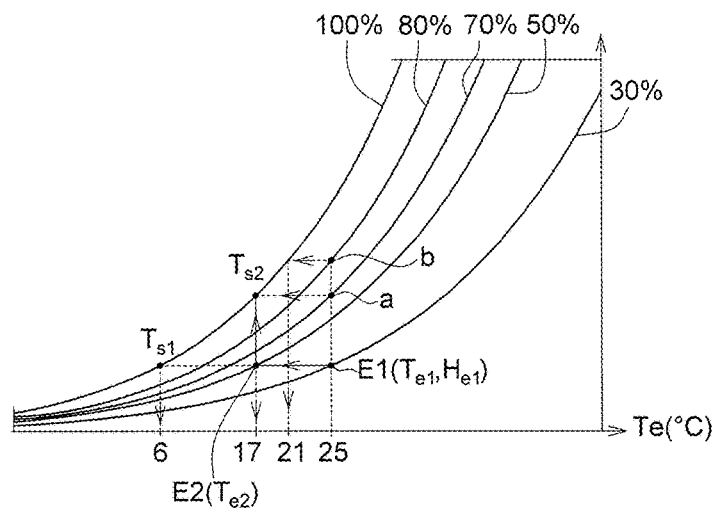
FIG. 3 is schematic diagram showing a diagram of a temperature and humidity curve according to an embodiment of the present disclosure.

In step S110, referring to FIGS. 1-3, FIG. 3 shows a diagram of a temperature and humidity curve according to an embodiment of the present disclosure. When the workpiece 10 is located at the first space SP1, the first air-conditioning module 110 provides the workpiece 10 with the first environment E1. The first air-conditioning module 110 includes a temperature controller and a humidity controller for controlling the temperature and the humidity of the first environment E1 at a first environmental temperature $T_{e1}$ and a first environmental relative humidity $H_{e1}$, wherein the first environmental temperature $T_{e1}$ is higher than a first saturation temperature $T_{s1}$ corresponding to the first environmental relative humidity $H_{e1}$. As a result, it can prevent water droplet from being condensed on the surface 10s of the workpiece 10. That is, due to the first environment E1 being a low humidity environment, it can prevent water droplet from being condensed on the surface 10s of the workpiece 10.

In detail, as shown in FIG. 3, in the example of the first environmental temperature $T_{e1}$ being 25° C., and the first environmental relative humidity $H_{e1}$ being 30%, due to 25° C. being higher than the first saturation temperature $T_{s1}$ corresponding to relative humidity 30%, that is, 6° C. (in horizontal dotted line toward left direction to correspond to 6° C.), the first environment E1 is at a lower humidity environment, such that it can prevent water droplet from being condensed on the surface 10s of the workpiece 10. However, as long as water droplet is prevented from being condensed on the surface 10s of the workpiece 10, the value of the first environmental temperature $T_{e1}$ and the value of the first environmental relative humidity $H_{e1}$ are not limited to the embodiment of the present disclosure.

In step S120, as shown in FIGS. 1 and 3, the workpiece 10 is moved to the second space S2, and the second air-conditioning module 120 provides the workpiece 10 with the second environment E2. The second air-conditioning module 120 may include a temperature controller and a humidity controller for controlling the temperature and the humidity of the second environment E2 at a second environmental temperature $T_{e2}$, wherein the second environmental temperature $T_{e2}$ is lower than the first environmental temperature $T_{e1}$ for reducing a itself-temperature $T_b$ to a mist temperature. In an embodiment, the mist temperature may be higher than the second environmental temperature $T_{e2}$, or equal to or approaches the second environmental temperature $T_{e2}$.

In step S130, whether the itself-temperature $T_b$ of the workpiece 10 reaches the mist temperature is detected by the temperature sensor 150, whether the temperature sensor 150 is, for example, non-contact infrared sensor or other non-contact temperature sensor. If the itself-temperature $T_b$ of the workpiece 10 reaches the mist temperature, the step S140 is performed; if not, the workpiece 10 may be maintained in the second environment E2 until the itself-temperature $T_b$ of the workpiece 10 is reduced to the mist temperature. In another embodiment, if the itself-temperature $T_b$ of the workpiece 10 has not reached to the mist temperature yet, the second air-conditioning module 120 may reduce the second environmental temperature $T_{e2}$ to make the workpiece 10 reach to the mist temperature more fast. The aforementioned mist temperature may depend on the mist saturation temperature $T_{sa}$ of the mist environment Ea; however, such exemplification is not meant to be for limiting.

In step S140, the mist air-conditioning module 130 provides the workpiece 10 with the mist environment Ea. The mist air-conditioning module 130 may include a temperature controller and a humidity controller for controlling the temperature and the humidity of the mist environment Ea at a mist-environmental relative humidity $H_{ea}$ and a mist-environmental temperature $T_{ea}$, wherein a mist-saturation temperature $T_{sa}$ corresponding to the mist-environmental relative humidity $H_{ea}$ is equal to or higher than the mist temperature for misting the surface 10s of the workpiece 10.

As shown in FIG. 3, in the example of the mist temperature being 17° C., if the mist-environmental temperature $T_{ea}$ is 25° C., the mist air-conditioning module 130 may humidify the mist environment Ea for increasing the mist-environmental relative humidity $H_{ea}$ to 70% (as shown by point "a" in FIG. 3). As a result, the mist-saturation temperature $T_{sa}$ corresponding to the relative humidity 70% is about 17° C., and accordingly the surface 10s of the workpiece 10 may be misted. In another embodiment, the mist air-conditioning module 130 may humidify the mist environment Ea for increasing the mist-environmental relative humidity $H_{ea}$ to be higher than 70%, for example, 80% (as shown by point "b" in FIG. 3). The mist-saturation temperature $T_{sa}$ (about 21° C.) corresponding to the relative humidity 80% is higher than 17° C., and accordingly the surface 10s of the workpiece 10 also may be misted. In addition, the aforementioned mist-environmental temperature $T_{ea}$ may be higher than the mist temperature, and it is not limited to 25° C.

Figure 4:
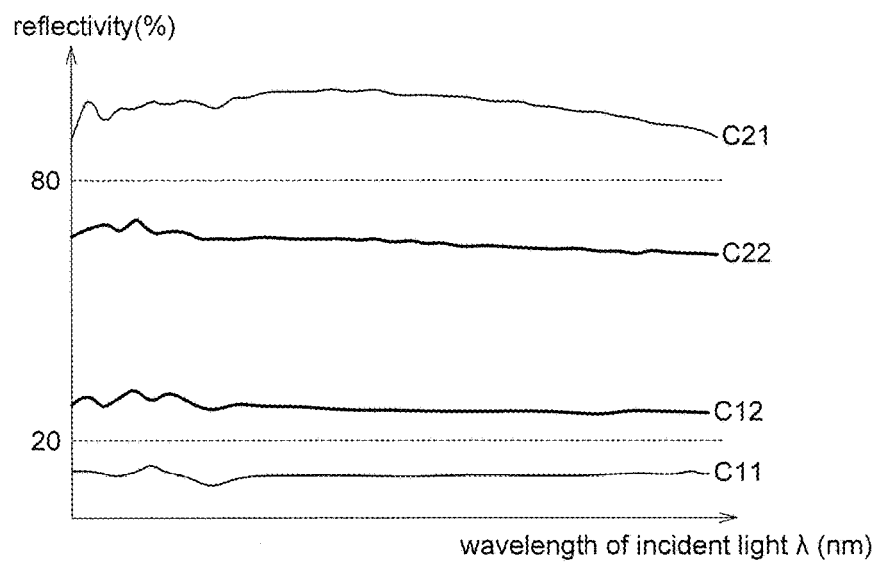
FIG. 4 is schematic diagram showing a curve of the measured reflectivity of the misted surface of the workpiece.

FIG. 4 is schematic diagram showing a curve of the reflectivity of the misted surface 10s of the workpiece 10. When the workpiece 10 is a transparent acrylic material with low light transmittance, according to the measured results, the reflectivity of the surface 10s of the workpiece 10 is less than 20% (as shown by the curve C11) before the surface 10s of the workpiece 10 is misted, but is higher than 20% (as shown by curve C12) after the surface 10s of the workpiece 10 is misted. When the workpiece 10 is a reflective sheet having a high light transmittance, according to the measured results, the reflectivity of the surface 10s of the workpiece 10 is higher than 80% (as shown by the curve C21) before the surface 10s of the workpiece 10 is misted, but is lower than 80% (as shown by curve C22) after the surface 10s of the workpiece 10 is misted.

In step S150, the detecting module 140 inspects and/or measures the misted surface 10s of the workpiece 10. For example, the detecting module 140 includes a robotic arm 141 and an optical detecting component 142, wherein the optical detecting component 142 is disposed on the robotic arm 141 for being driven by the robotic arm 141 to scan the three-dimensional contours of the surface 10s of the workpiece 10 or inspect whether the surface 10s has defects. In addition, the detecting module 140 may inspects and/or measures the workpiece 10 within or outside the mist space SP3.

Figure 5:
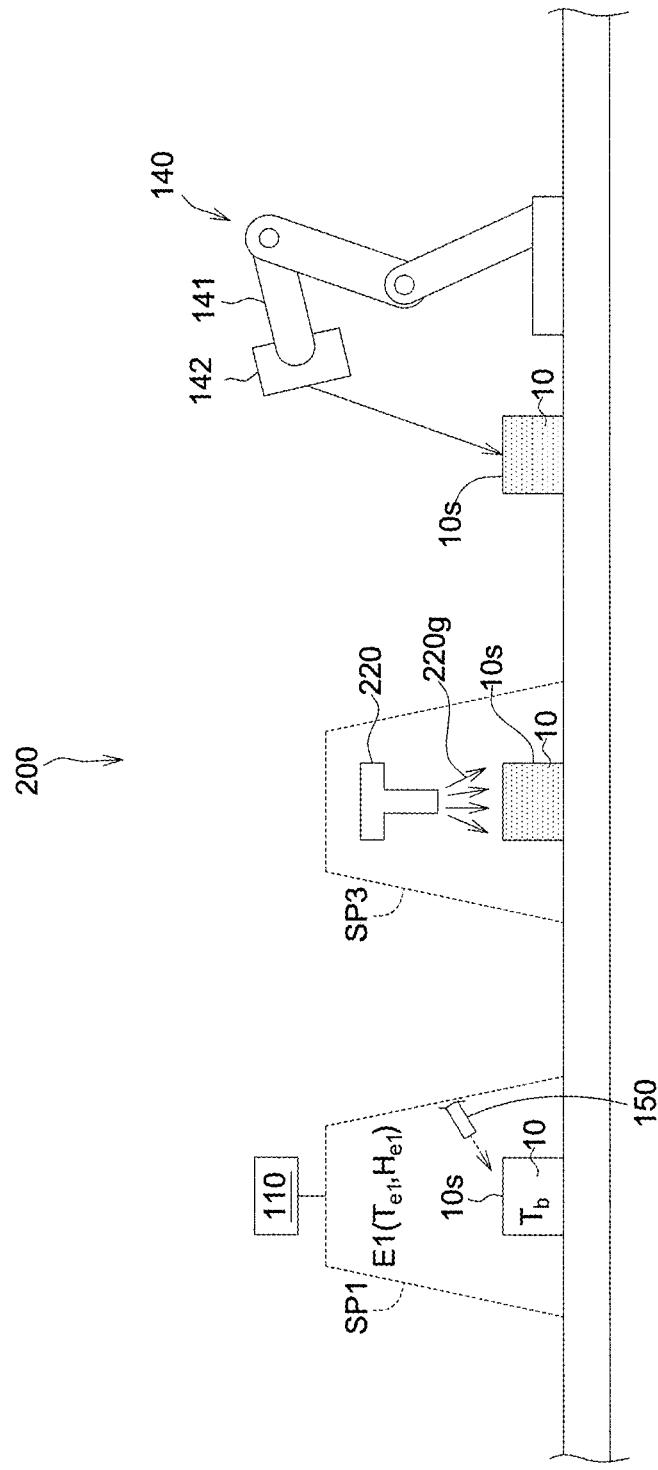
FIG. 5 is schematic diagram showing a diagram of a detecting system for a workpiece surface according to another embodiment of the present disclosure.

FIG. 5 is schematic diagram showing a diagram of a detecting system 200 for a workpiece surface according to another embodiment of the present disclosure. The detecting system 200 includes the first air-conditioning module 110, a gas provider 220, the detecting module 140 and the temperature sensor 150. The present embodiment is different from above embodiment in that the gas provider 220 provides the workpiece 10 with mist environment.

Figure 6:
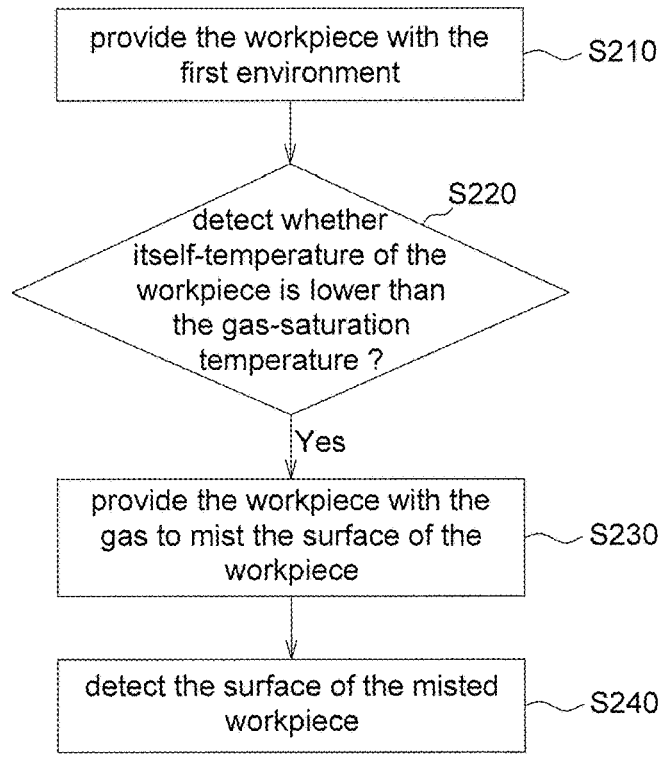
FIG. 6 is schematic diagram showing a flowchart of a detecting method for a workpiece surface according to another embodiment of the present disclosure.

FIG. 6 is schematic diagram showing a flowchart of an detecting method for a workpiece surface according to another embodiment of the present disclosure.

Figure 7:
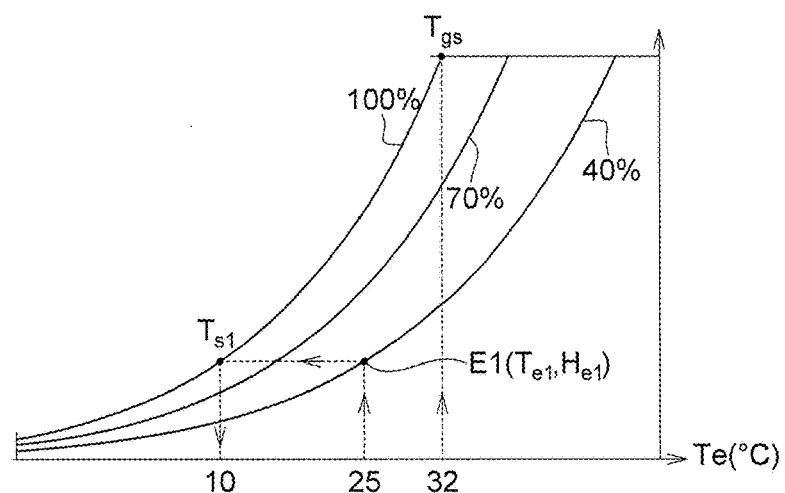
FIG. 7 is schematic diagram showing a diagram of a temperature and humidity curve according to an embodiment of the present disclosure.

In step S210, and referring to FIG. 7, FIG. 7 is schematic diagram showing a diagram of a temperature and humidity curve according to another embodiment of the present disclosure. When the workpiece 10 is located at the first space SP1, the first air-conditioning module 110 provides the workpiece 10 with the first environment E1. For example, the first air-conditioning module 110 includes the temperature controller and the humidity controller for controlling the temperature and the humidity of the first environment E1 at the first environmental temperature $T_{e1}$ and the first environmental relative humidity $H_{e1}$ respectively, wherein the first environmental temperature $T_{e1}$ is higher than the first saturation temperature $T_{s1}$ corresponding to the first environmental relative humidity $H_{e1}$. Due to the first environmental temperature $T_{e1}$, the itself-temperature $T_b$ of the workpiece 10 approaches the first environmental temperature $T_{e1}$, wherein due to the first environmental temperature $T_{e1}$ being higher than the first saturation temperature $T_{s1}$, the itself-temperature $T_b$ of the workpiece 10 is also higher than the first saturation temperature $T_{s1}$. Since the itself-temperature $T_b$ of the workpiece 10 is higher than the first saturation temperature $T_{s1}$, water droplet is prevented from being condensed on the surface 10s of the workpiece 10, and mist uniformity of the surface 10s of the workpiece 10 will not be affected by water droplet. For example, as shown in FIG. 7, in the example of the first environmental temperature $T_{e1}$ being 25° C. and the first environmental relative humidity $H_{e1}$ being 40%, the first saturation temperature $T_{s1}$ is 10° C. Thus, as long as the itself-temperature $T_b$ of the workpiece 10 is higher than 10° C., it can prevent water droplet from being condensed on the surface 10s of the workpiece 10. However, as long as water droplet is prevented from being condensed on the surface 10s of the workpiece 10, the value of the first saturation temperature $T_{s1}$ and value of the first environmental relative humidity $H_{e1}$ are not limited to the present embodiment.

In addition, since the first environmental relative humidity $H_{e1}$ may be controlled to be lower than the relative humidity outside the first environment E1, the first environment E1 is at a low humidity environment. As a result, even if there is water droplet at the surface 10s of the workpiece 10, the water droplet will evaporate due to the low humidity environment.

In step S220, whether the itself-temperature $T_b$ of the workpiece 10 is lower than the gas-saturation temperature $T_{ga}$ of the gas 220g (shown in FIG. 5) is detected by the temperature sensor 150, whether the temperature sensor 150 is, for example, non-contact infrared sensor or other non-contact temperature sensor. If the itself-temperature $T_b$ of the workpiece 10 is lower than the gas-saturation temperature $T_{ga}$, the step S230 is performed; if not, the workpiece 10 may be maintained in the first environment E1 until the itself-temperature $T_b$ of the workpiece 10 is lower than the gas-saturation temperature $T_{ga}$. Alternatively, the itself-temperature $T_b$ of the workpiece 10 may be much rapidly reduced to be lower than the gas-saturation temperature $T_{ga}$ of the gas 220g by way of reducing the first environmental temperature $T_{e1}$.

In step S230, the gas provider 220 provides the workpiece 10 with the mist environment Ea. For example, the gas provider 220 provides the workpiece 10 with the aforementioned gas 220g. The gas 220g is, for example, vapor or mixture of vapor and gas. The gas provider 220 is, for example, an evaporator, sprayer, or other gas provider capable of providing various temperatures and/or relative humidity. In the example of the relative humidity $H_{eg}$ of the gas 220g being 100%, as shown in FIG. 7, due to the gas-saturation temperature $T_{gs}$ is equal to or higher than the itself-temperature $T_b$ of the workpiece 10, the surface 10s of the workpiece 10 may be misted. For example, in the example of the gas-saturation temperature $T_{gs}$ of the gas 220g being 32° C., since 32° C. is higher than the itself-temperature $T_b$ of the workpiece 10 which is 25° C., for example, and accordingly the surface 10s of the workpiece 10 may be misted. In detail, the gas-saturation temperature $T_{gs}$ of the gas 220g is higher than the itself-temperature $T_b$ of the workpiece 10, and accordingly the gas 220g will be condensed on the surface 10s of the workpiece 10 when being contacting with the surface 10s. In addition, the gas 220g may include several fine water droplets each having a diameter of 0.1 micrometers to 2 micrometers, such that the surface 10s forms a misted surface.

In step S240, the detecting module 140 inspects and/or measures the misted surface 10s of the workpiece 10. For example, the detecting module 140 includes the robotic arm 141 and the optical detecting component 142 disposed on the robotic arm 141 for being driven by the robotic arm 141 to scan the three-dimensional contours of the surface 10s of the workpiece 10 or inspect whether the surface 10s has defects. In addition, the detecting module 140 may inspects and/or measures the workpiece 10 within or outside the mist space SP3.

As described above, an detecting method of an embodiment of the present disclosure provides a dry process (for example, the aforementioned first environment), a cooling process (for example, the aforementioned second environment) and a humidifying and misting process (for example, the aforementioned mist environment), wherein the fine water droplet (misted) is condensed on the surface of the workpiece in the last humidifying and misting process. In another embodiment, a detecting method provides a dry process (for example, the aforementioned first environment) and a gas, wherein the gas-saturation temperature of the gas is higher than a itself-temperature of the workpiece, such that the surface of the workpiece is misted when the gas contacts the surface of the workpiece having relative low temperature and then is condensed.

It will be apparent to those skilled in the art that various modifications and variations can be made to the structure of the disclosed embodiments without departing from the scope or spirit of the disclosure. In view of the foregoing, it is intended that the disclosure cover modifications and variations of the present disclosure provided they fall within the scope of the following claims and their equivalents.

What is claimed is:

1. A detecting method for a workpiece surface, comprising:

providing a workpiece with a first environment, wherein the first environment has a first environmental temperature higher than a first saturation temperature corresponding to a first environmental-relative humidity of the first environment;

providing the workpiece with a second environment, wherein the second environment has a second environmental temperature lower than the first environmental temperature, such that an itself-temperature of the workpiece reduces to a mist temperature, wherein the mist temperature is substantially equal to or higher than the second environmental temperature;

providing the workpiece with a mist environment, wherein the mist environment has a mist-saturation temperature corresponding to a mist-environment-relative humidity is equal to or higher than the temperature for misting a surface of the workpiece; and detecting the surface of the misted workpiece.

2. The detecting method according to claim 1, wherein the surface of the misted workpiece is detected by way of non-contact.

3. The detecting method according to claim 1, wherein the step of providing the workpiece with the first environment is completed in a first space; after the step of providing the workpiece with the first environment, the detecting method further comprises:

transporting the workpiece to a second space to perform the step of providing the workpiece with the second environment; and transporting the workpiece to a mist space to perform the step of providing the workpiece with the mist environment.

4. The detecting method according to claim 1, wherein the step of providing the workpiece with the first environment, the step of providing the workpiece with the second environment and the step of providing the workpiece with the mist environment are completed in the same space.

5. A detecting system for a workpiece surface, comprising:

a first air-conditioning module configured to provide a workpiece with a first environment, wherein the first environment has a first environmental temperature higher than a first saturation temperature corresponding to a first environmental-relative humidity of the first environment;

a second air-conditioning module configured to provide the workpiece with a second environment, wherein the second environment has a second environmental temperature lower than the first environmental temperature, such that an itself-temperature of the workpiece reduces to a mist temperature, wherein the mist temperature is substantially equal to or higher than the second environmental temperature;

a mist air-conditioning module configured to the workpiece with a mist environment, wherein the mist environment has a mist-saturation temperature corresponding to a mist-environmental relative humidity is equal to or higher than the mist temperature for misting a surface of the workpiece; and a detecting module configured to detect the surface of the misted workpiece.

6. The detecting system according to claim 5, wherein the first air-conditioning module, the second air-conditioning module and the mist air-conditioning module are integrated into single air-conditioning module.

7. The detecting system according to claim 5, wherein the first environment, the second environment and the mist environment are in the same space.

8. The detecting system according to claim 5, wherein the first environment, the second environment and the mist environment are in a first space, a second space and a mist space respectively, and the first space, the second space and the mist space are different spaces.

9. The detecting system according to claim 5, further comprising:

a temperature sensor configured to detect whether the itself-temperature of the workpiece reaches the mist temperature.

* * * * *